United States Patent [19]
Hagmann et al.

[11] Patent Number: 5,866,545
[45] Date of Patent: Feb. 2, 1999

[54] SUBSTITUTED KETONE DERIVATIVES AS INHIBITORS OF INTERLEUKIN-1β CONVERTING ENZYME

[75] Inventors: William K. Hagmann, Westfield; Justin J. Zhao, Jersey City; Malcolm MacCoss, Freehold, all of N.J.; Adnan M. Mjalli, San Diego, Calif.

[73] Assignee: Merck & Co., Inc., Rahway, N.J.

[21] Appl. No.: 578,613

[22] PCT Filed: Aug. 8, 1994

[86] PCT No.: PCT/US94/08868

§ 371 Date: Jan. 11, 1996

§ 102(e) Date: Jan. 11, 1996

[87] PCT Pub. No.: WO95/05192

PCT Pub. Date: Feb. 23, 1995

Related U.S. Application Data

[63] Continuation-in-part of Ser. No. 106,468, Aug. 13, 1993, abandoned.

[51] Int. Cl.$^6$ .............................. A61K 38/00; C07K 5/00
[52] U.S. Cl. .............................. 514/18; 514/19; 530/330; 530/331; 562/571
[58] Field of Search ........................ 514/18, 19; 530/330, 530/331; 562/571

[56] References Cited

U.S. PATENT DOCUMENTS

| | | | |
|---|---|---|---|
| 4,481,192 | 11/1984 | Cazaubon et al. | 514/18 |
| 4,582,821 | 4/1986 | Kettner et al. | 514/18 |
| 5,055,451 | 10/1991 | Krantz et al. | 514/19 |
| 5,169,935 | 12/1992 | Hoeger et al. | 530/328 |
| 5,283,293 | 2/1994 | Webb | 525/332.2 |
| 5,324,833 | 6/1994 | Sieber et al. | 544/183 |

FOREIGN PATENT DOCUMENTS

| | | |
|---|---|---|
| 0 263 202 | 4/1988 | European Pat. Off. . |
| WO 91/15577 | 10/1991 | WIPO . |
| WO 93/09135 | 5/1993 | WIPO . |

OTHER PUBLICATIONS

Banerjee, et al Chem. Abstracts vol. 92 (17), p. 633 Ab #147159s (1980).
Black, et al, J. Biol. Chem. vol. 263, pp. 9437–9442 (1988).
Black, et al, J. Biol. Chem. vol. 264, pp. 5323–5326, (1988).
Black, et al, Feb. Lett. vol. 247, pp. 286–290 (1989).
Howard, et al, J. Immunology vol. 147, pp. 2964–2969 (1991).
Kostura, et al, Proc. Natl. Acad. Sci. vol. 86, pp. 5227–5231 (1989).
Moon, et al, J. Am. Chem. Soc. vol. 198, pp. 1350–1351 (1986).
Pat Abstr. of Japan, vol. 13 (227) (C–600) (3575) (May 25, 1989).
Ressler, et al, J. Org. Chem. vol. 36 (25), pp. 3960–3966 (1971).
Sleath, et al, J. Biol. Chem. vol. 265, pp. 14526–14528 (1990).
Thornberry, et al, Nature, vol. 356, pp. 768–774 (Apr. 30, 1992).
Weidner, et al, Peptides, Chemistry, Biology, Proceeding of the 12th American Peptide Symposium, Jun. 16–21, 1991 Cambridge, Mass., USA pp. 891–892 (1992).
Gross, The Peptides, vol. 3, pp. 101–104 (1981).

*Primary Examiner*—Cecilia J. Tsang
*Assistant Examiner*—Bennett Celsa
*Attorney, Agent, or Firm*—Curtis C. Panzer; David L. Rose

[57] ABSTRACT

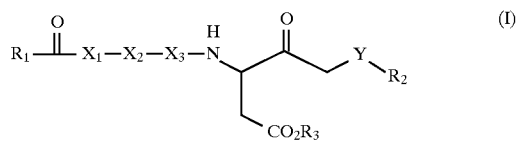

This invention relates to substituted ketone derivatives of formula (I) useful in the treatment of inflammation in lung, central nervous system, kidney, joints, endocardium, pericardium, eyes, ears, skin, gastrointestinal tract and urogenital system. More particularly, this invention relates to substituted ketone drivatives that are useful inhibitors of interleukin-1β converting enzyme (ICE). Interleukin-1β converting enzyme (ICE) has been identified as the enzyme responsible for converting precursor interleukin-1β (IL-1β) to biologically active IL-1β.

7 Claims, No Drawings

SUBSTITUTED KETONE DERIVATIVES AS INHIBITORS OF INTERLEUKIN-1β CONVERTING ENZYME

This application is a 371 of PCT/US94/08868 filed Aug. 8, 1994 which is a CIP of application Ser. No. 08/106,468 filed Aug. 13, 1993.

BACKGROUND OF THE INVENTION

This invention relates to substituted ketone derivatives of Formula I useful in the treatment of inflammation in lung, central nervous system, kidney, joints, endocardium, pericardium, eyes, ears, skin, gastro-intestinal tract and urogenital system. More particularly, this invention relates to substituted ketone derivatives that are useful inhibitors of interleukin-1β converting enzyme (ICE). Interleukin-1β converting enzyme (ICE) has been identified as the enzyme responsible for converting precursor interleukin-1β (IL-1β) to biologically active IL-1β.

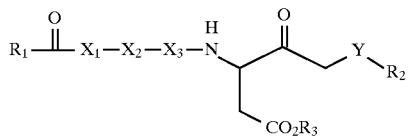

Mammalian interleukin-1 (IL-1) is an immunoregulatory protein secreted by cell types as part of the inflammatory response. The primary cell type responsible for IL-1 production is the peripheral blood mono-cyte. Other cell types have also been described as releasing or containing IL-I or IL-I like molecules. These include epithelial cells (Luger, et al., J. Immunol. 127: 1493–1498 (1981), Le et al., J. Immunol. 138: 2520–2526 (1987) and Lovett and Larsen, J. Clin. Invest. 82: 115–122 (1988), connective tissue cells (Ollivierre et al., Biochem. Biophys. Res. Comm. 141: 904–911 (1986), Le et al, J. Immunol. 138: 2520–2526 (1987), cells of neuronal origin (Giulian et al., J. Esp. Med. 164: 594–604 (1986) and leukocytes (Pistoia et al., J. Immunol. 136: 1688–1692 (1986), Acres et al., Mol. Immuno. 24: 479–485 (1987), Acres et al., J. Immunol. 138: 2132–2136 (1987) and Lindenmann et al., J. Immunol 140: 837–839 (1988).

Biologically active IL-I exists in two distinct forms, IL-1α with an isoelectric point of about pI 5.2 and IL-1β2 with an isoelectric point of about 7.0 with both forms having a molecular mass of about 17.5 kDa (Bayne et al., J. Exp. Med. 163: 1267–1280 (1986) and Schmidt, J. Exp. Med. 160: 772 (1984). The polypeptides appear evolutionarily conserved, showing about 27–33% homology at the amino acid level (Clark et al., Nucleic Acids Res. 14: 7897–7914 (1986).

Mammalian IL-1β is synthesized as a cell associated precursor polypeptide with a molecular mass of about 31 kDa (Limjuco et al., Proc. Natl. Acad. Sci USA 83: 3972–3976 (1986). Precursor IL-1β is unable to bind to IL-1 receptors and is biologically inactive (Mosley et al., J. Biol. Chem. 262: 2941–2944 (1987). Biological activity appears dependent upon some form of proteolytic processing which results in the conversion of the precursor 31 kDa form to the mature 17.5 kDa form. Evidence is growing that by inhibiting the conversion of precursor IL-1β to mature IL-1β, one can effectively inhibit the activity of interleukin-1.

Mammalian cells capable of producing IL-1β include, but are not limited to, keratinocytes, endothelial cells, mesangial cells, thymic epithelial cells, dermal fibroblasts, chondrocytes, astrocytes, glioma cells, mono-nuclear phagocytes, granulocytes, T and B lymphocytes and natural killer cells.

As discussed by J. J. Oppenheim, et al., Immunology Today, vol. 7(2):45–56 (1986), the activities of interleukin-1 are many. It has been observed that catabolin, a factor that promotes degradation of cartilage matrix, also exhibited the thymocyte co-mitogenic activities of IL-1 and stimulates chondrocytes to release matrix metalloproteinases and plasminogen activator. In addition, a plasma factor termed 'proteolysis inducing factor' stimulates muscle cells to produce prostaglandins which in turn leads to proteolysis, the release of amino acids and, in the long run, muscle wasting, and appears to represent a fragment of IL-1 with fever-inducing, acute phase response and thymocyte co-mitogenic activities.

IL-1 has multiple effects on cells involved in inflammation and wound healing. Subcutaneous injection of IL-1 leads to margination of neutrophils and maximal extravascular infiltration of the polymorphonuclear leukocytes (PMN). In vitro studies reveal IL-1 to be a chemotactic attractant for PMN, to activate PMN to metabolize glucose more rapidly, to reduce nitroblue tetrazolium, and to release PMN lysozomal enzymes. Endothelial cells are stimulated to proliferate by IL-1 to produce thromboxane, to become more adhesive, and to release procoagulating activities. IL-1 also enhances collagen type IV production by epidermal cells, induces osteoblast proliferation and alkaline phosphatase production, and stimulates osteoclasts to resorb bone. Even macrophages have been reported to be chemotactically attracted to IL-1 to produce prostaglandins in response to IL-1 and to exhibit a more prolonged and active tumoricidal state.

IL-1 is also a potent bone resorptive agent which upon infusion into mice causes hypercalcemia and increases in bone resorptive surface as revealed by histomorphometry (Sabatini, M. et al., PNAS 85:5235–5239, 1988).

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, interstitial nephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix. Such diseases include periodontal diseases, interstitial pulmonary fibrosis, cirrhosis, systemic sclerosis, and keloid formation. ICE inhibitors of Formula I may also be useful in treatment of certain tumors which produce IL-1 as an autocrine growth factor and in preventing the cachexia associated with certain tumors.

SUMMARY OF THE INVENTION

Novel ketone derivatives of Formula I are found to be potent inhibitors of interleukin-1β converting enzyme (ICE).

Compounds of Formula I are useful in the treatment of deseases including inflammation in lung, central nervous system, kidney, joints, endocardium, pericardium, eyes, ears, skin, gastrointestinal tract and urogenital system.

DETAILED DESCRIPTION OF THE INVENTION

The invention encompasses compounds of Formula I.

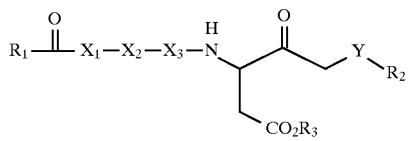

or a pharmaceutically acceptable salt thereof thereof:
wherein:
$R_1$ is
  (a) substituted $C_{1-6}$alkyl or substituted $C_{1-6}$alkoxy, wherein the substituent is selected from
    (1) hydrogen,
    (2) hydroxy,
    (3) halo which is defined to include F, Br, Cl, and I,
    (4) $C_{1-3}$alkyloxy,
    (5) $C_{1-3}$alkylthio,
    (6) phenyl $C_{1-3}$alkyloxy, and
    (7) phenyl $C_{1-3}$alkylthio;
  (b) substituted $C_{2-6}$ alkenyl or substituted $C_{2-6}$ alkenyloxy, wherein the substituent is selected from
    (1) hydrogen,
    (2) hydroxy,
    (3) halo,
    (4) $C_{1-3}$alkyloxy,
    (5) $C_{1-3}$alkylthio,
    (6) phenyl $C_{1-3}$alkyloxy, and
    (7) phenyl $C_{1-3}$alkylthio;
  (c) aryl, aryl $C_{1-6}$alkyl, and aryl $C_{2-6}$alkyloxy wherein the $C_{1-6}$alkyl is optionally substituted with $C_{1-3}$alkylcarbonylamino, and the aryl group is selected from the group consisting of:
    (1) phenyl,
    (2) naphthyl,
    (3) pyridyl,
    (4) furyl,
    (5) pyrryl,
    (6) thienyl,
    (7) isothiazolyl,
    (8) imidazolyl,
    (9) benzimidazolyl,
    (10) tetrazolyl,
    (11) pyrazinyl,
    (12) pyrimidyl,
    (13) quinolyl,
    (14) isoquinolyl,
    (15) benzofuryl,
    (16) isobenzofuryl,
    (17) benzothienyl,
    (18) pyrazolyl,
    (19) indolyl,
    (20) isoindolyl,
    (21) purinyl,
    (22) carbazolyl,
    (23) isoxazolyl,
    (24) thiazolyl,
    (25) oxazolyl,
    (26) benzthiazolyl, and
    (27) benzoxazolyl, and mono- and di-substituted aryl as defined above in items (1) to (27) wherein the substitutents on the aryl are independently selected from $C_{1-6}$alkyl, $C_{1-6}$alkyloxy, halo, hydroxy, amino, $C_{1-6}$alkylamino, amino $C_{1-6}$alkyl, carboxyl, carboxyl $C_{1-6}$alkyl, and $C_{1-6}$alkylcarbonyl;

$R_2$ is
  (a) phenyl,
  (b) 1-naphthyl,
  (c) substituted 2-naphthyl wherein the substituents are individually selected from the group consisting of
    (1) hydrogen,
    (2) halo,
    (3) $C_{1-6}$alkyl,
    (4) perfluoro $C_{1-3}$alkyl,
    (5) nitro,
    (6) cyano,
    (7) $C_{1-6}$alkylcarbonyl,
    (8) phenylcarbonyl,
    (9) carboxy,
    (10) aminocarbonyl,
    (11) mono- and di-$C_{1-6}$alkylaminocarbonyl,
    (12) phenylaminocarbonyl,
    (13) formyl,
    (14) aminosulfonyl,
    (15) $C_{1-6}$alkyl sulfonyl,
    (16) phenyl sulfonyl,
    (17) formamido,
    (18) $C_{1-6}$alkylcarbonylamino,
    (19) phenylcarbonylamino,
    (20) $C_{1-6}$alkoxycarbonyl,
    (21) $C_{1-6}$alkylsulfonamido carbonyl,
    (22) phenylsulfonamido carbonyl,
    (23) $C_{1-6}$alkyl carbonylamino sulfonyl,
    (24) phenylcarbonylamino sulfonyl,
    (25) $C_{1-6}$alkyl amino,
    (26) $C_{1-3}$dialkyl amino,
    (27) amino,
    (28) hydroxy,
    (29) $C_{1-6}$alkyloxy, and
    (30) aryl, aryl $C_{1-6}$alkyl, and aryl $C_{1-6}$alkoxy wherein the aryl group is selected from the group consisting of:
      (a) phenyl,
      (b) naphthyl,
      (c) pyridyl,
      (d) furyl,
      (e) pyrryl,
      (f) thienyl,
      (g) isothiazolyl,
      (h) imidazolyl,
      (i) benzimidazolyl,
      (j) tetrazolyl,
      (k) pyrazinyl,
      (l) pyrimidyl,
      (m) quinolyl,
      (n) isoquinolyl,
      (o) benzofuryl,
      (p) isobenzofuryl,
      (q) benzothienyl,
      (r) pyrazolyl,
      (s) indolyl,
      (t) isoindolyl, (u) purinyl,
(v) carbazolyl,
(w) isoxazolyl,
(x) thiazolyl,
(y) oxazolyl,
(z) benzthiazolyl, and
(a1) benzoxazolyl, and mono- and di-substituted aryl or heteroaryl as defined above in items (a) to (a1) wherein the substitutents are independently selected from $C_{1-6}$alkyl, $C_{1-6}$alkyloxy, halo, hydroxy, amino, $C_{1-6}$alkylamino, amino $C_{1-6}$alkyl, carboxyl, carboxyl $C_{1-6}$alkyl, and $C_{1-6}$alkylcarbonyl;

$R_3$ is
(a) hydrogen,
(b) $C_{1-6}$alkyl,
(c) phenyl and phenyl $C_{1-6}$alkyl, and mono- and di-substituted phenyl wherein the substitutents are independently selected from $C_{1-6}$alkyl, $C_{1-6}$alkyloxy, halo, hydroxy, amino, $C_{1-6}$alkylamino, amino $C_{1-6}$alkyl, carboxyl, carboxyl $C_{1-6}$alkyl, and $C_{1-6}$alkylcarbonyl;

$X_1$ is selected from the group consisting of
(a) a single bond, and
(b) an amino acid of Formula II

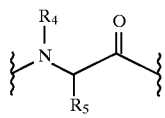

II $X_2$ is selected from the group consisting of
(a) a single bond, and
(b) an amino acid of Formula III

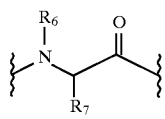

III $X_3$ is selected from the group consisting of
(a) a single bond, and
(b) an amino acid of Formula II

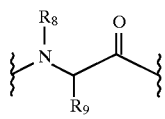

IV wherein $R_4$, $R_5$, $R_6$, $R_7$, $R_8$ and $R_9$ are independently selected from the group consisting of:
(a) hydrogen,
(b) substituted $C_{1-6}$alkyl, wherein the substituent is selected from
(1) hydrogen,
(2) hydroxy,
(3) halo,
(4) $C_{1-3}$alkylthio,
(5) thiol,
(6) $C_{1-6}$alkylcarbonyl,
(7) carboxy,
(8) aminocarbonyl,
(9) amino carbonyl amino,
(10) amino,
(11) $C_{1-3}$alkylamino, wherein the alkyl moiety is substituted with hydrogen or hydroxy, and
(12) guanidino;
(c) aryl and aryl $C_{1-6}$alkyl wherein the aryl group is selected from the group consisting of:
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) thiazolyl,
(25) oxazolyl,
(26) benzthiazolyl, and
(27) benzoxazolyl,
and mono- and di-substituted aryl or heteroaryl as defined above in items (1) to (27) wherein the substitutents are independently selected from $C_{1-6}$alkyl, $C_{1-6}$alkyloxy, halo, hydroxy, amino, $C_{1-6}$alkylamino, amino $C_{1-6}$alkyl, carboxyl, carboxyl $C_{1-6}$alkyl, and $C_{1-6}$alkylcarbonyl;
(d) $R_4$ and $R_5$, $R_6$ and $R_7$, and $R_8$ and $R_9$ may be joined, such that together with the nitrogen atom to which $R_4$ (or $R_6$ or $R_8$) is attached there is formed a mono-cyclic saturated ring of 5 to 8 atoms, said ring having exactly one hetero atom which is nitrogen, said ring optionally having an oxo group, said ring including,

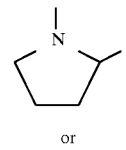

or

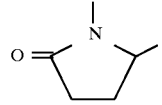

Y is O, S, or NH.

One class of this genus is the compounds wherein:
$R_1$ is
(a) substituted $C_{1-6}$alkyl or substituted $C_{1-6}$alkoxy, wherein the substituent is selected from
(1) hydrogen,
(2) hydroxy,
(3) chloro or fluoro,
(4) $C_{1-3}$alkyloxy, and
(5) phenyl $C_{1-3}$alkyloxy,
(b) aryl $C_{1-6}$alkyl wherein the aryl group is selected from the group consisting of (1) phenyl,
(2) naphthyl,
(3) pyridyl,
(4) furyl,
(5) thienyl,
(6) thiazolyl,
(7) isothiazolyl,
(8) benzofuryl,
(9) benzothienyl,
(10) indolyl,
(11) isooxazolyl, and
(12) oxazolyl, and mono- and di-substituted aryl as defined above in items (1) to (12) wherein the substitutents are independently $C_{1-4}$alkyl, halo, and hydroxy;

$R_4$ is hydrogen and $R_5$ is selected from the group consisting of
(a) hydrogen,
(b) substituted $C_{1-6}$alkyl, wherein the substituent is selected from
  (1) hydrogen,
  (2) hydroxy,
  (3) halo,
  (4) $C_{1-4}$alkyl thio
  (5) thiol
  (6) $C_{1-6}$alkylcarbonyl,
  (7) carboxy,
  (8) aminocarbonyl,
  (9) $C_{1-4}$alkylamino, and $C_{1-4}$alkylamino wherein the alkyl moiety is substituted with an hydroxy, and
  (10) guanidino,
  (11) $C_{1-4}$alkyloxy,
  (12) phenyl $C_{1-4}$alkyloxy,
  (13) phenyl $C_{1-4}$alkylthio, and
(c) aryl $C_{1-6}$alkyl, wherein the aryl group is elected from the group consisting of
  (1) phenyl,
  (2) naphthyl,
  (3) pyridyl,
  (4) furyl,
  (5) thienyl,
  (6) thiazolyl,
  (7) isothiazolyl,
  (8) benzofuryl,
  (9) benzothienyl,
  (10) indolyl,
  (11) isooxazolyl, and
  (12) oxazolyl, and wherein the aryl may be mono- and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$R_6$, $R_7$, $R_8$ and $R_9$ are each independently selected from the group consisting of
(a) hydrogen,
(b) $C_{1-6}$ alkyl, wherein the substituent is selected from
  (1) hydrogen,
  (2) hydroxy,
  (3) halo,
  (4) —S—$C_{1-4}$alkyl,
  (5) —SH,
  (6) $C_{1-6}$alkylcarbonyl,
  (7) carboxy,
  (8) aminocarbonyl,
  (9) $C_{1-4}$alkylamino, and $C_{1-4}$alkyl amino wherein the alkyl moiety is substituted with an hydroxy, and
  (10) guanidino, and
(c) aryl $C_{1-6}$alkyl, wherein aryl is defined as immediately above, and wherein the aryl may be mono- and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

Within this class are the compounds wherein $X_1$, $X_2$ and $X_3$, are each independently selected from the group consisting of the L- and D- forms of the amino acids including glycine, alanine, valine, leucine, isoleucine, serine, threonine, aspartic acid, asparagine, glutamic acid, glutamine, lysine, hydroxy-lysine, histidine, arginine, phenyl-alanine, tyrosine, tryptophan, cysteine, methionine, ornithine, β-alanine, homoserine, homotyrosine, homophenylalanine and citrulline.

Alternatively, within this class are the subclass of compounds wherein $R_1$ is $C_{1-3}$alkyl, $C_{1-3}$alkenyl, $C_{1-3}$alkoxy or $C_{1-3}$alkenyloxy;

$R_6$, $R_7$, $R_8$ and $R_9$ are each individually
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(g) aminocarbonyl $C_{1-6}$alkyl,
(h) mono—or di-$C_{1-6}$alkyl amino $C_{1-6}$alkyl,
(i) guanidino $C_{1-6}$alkyl,
(j) amino-$C_{1-6}$alkyl or N-substituted amino-$C_{1-6}$alkyl wherein the substituent is carbobenzoxy,
(k) carbamyl $C_{1-6}$alkyl, or
(l) aryl $C_{1-6}$alkyl, wherein the aryl group is selected from phenyl and indolyl, and the aryl group may be substituted with hydroxy, $C_{1-3}$ alkyl.

Exemplifying the invention are the following compounds:
a) N-Allyloxycarbonyl-3-amino-4-oxo-5-phenoxypentanoic acid.
b) N-Allyloxycarbonyl-3-amino-5-(1-naphthyloxy)-4-oxopentanoic acid.
c) N-Allyloxycarbonyl-3-amino-5-(2-naphthyloxy)-4-oxopentanoic acid.
d) N-Allyloxycarbonyl-3-amino-5-(3-aminocarbonyl-2-naphthyloxy)-4-oxopentanoic acid.
e) N-Allyloxycarbonyl-3-amino-5-(3-(N-phenyl)aminocarbonyl-2-naphthyloxy)-4-oxopentanoic acid.
f) N-Allyloxycarbonyl-3-amino-5-(3-cyano-2-naphthyloxy)-4-oxopentanoic acid.
g) N-Allyloxycarbonyl-3-amino-5-(3-hydroxymethyl-2-naphthyloxy)-4-oxopentanoic acid.
h) N-Allyloxycarbonyl-3-amino-5-(3-methoxycarbonyl-2-naphthyloxy)-4-oxopentanoic acid.
i) N-Allyloxycarbonyl-3-amino-5-(3-imidazolyl-2-naphthyloxy)-4-oxopentanoic acid.
j) N-(N-Acetyl-(L)-tyrosinyl-(L)-valinyl-(L)-alaninyl)-3-amino-5-phenoxy-4-oxopentanoic acid.
k) N-(N-Carbobenzyloxy-(L)-valinyl-(L)-alaninyl)-3-amino-5-(3-aminocarbonyl-naphthyl-2-oxy)-4-oxopentanoic acid, triethylamine salt.
l) N-(N-Carbobenzyloxy-(L)-valinyl-(L)-prolinyl)-3-amino-5-(3-aminocarbonyl-naphthyl-2-oxy)-4-oxopentanoic acid.
m) N-(2-indoloyl)-3-amino-5-(3-aminocarbonyl-naphthyl-2-oxy)-4-oxo-pentanoic acid.

This invention also concerns to pharmaceutical composition and methods of treatment of interleukin-1 and interleukin-1β mediated or implicated disorders or diseases (as described above) in a patient (including man and/or mammalian animals raised in the dairy, meat, or fur industries or as pets) in need of such treatment comprising administration of interleukin-1β inhibitors of Formula (I) as the active constituents.

Illustrative of these aspects, this invention concerns pharmaceutical compositions and methods of treatment of diseases selected from septic shock, allograft rejection, inflammatory bowel disease and rheumatoid arthritis in a patient in need of such treatment comprising:

administration of an interleukin-1β converting enzyme inhibitor of Formula (I) as the active constituent.

Compounds of the instant invention have are particularly useful in the treatment of ICE mediated diseases advantageously treated with agents that are selective inhibitors of ICE. For example, structurally related compounds such as those disclosed in U.S. Pat. No. 5,055,451, issued to Krantz et. al., Oct. 8, 1991 by design inhibit cathepsin B. Compounds of the instant invention are selective inhibitors of ICE over Catiepsin B. For purposes of this specification a compound is to be considered selective for ICE over Cathepsin B if the ratios of the $IC_{50}$ for ICE to the $IC_{50}$ for Cathepsin B is 0.01 or smaller.

Compounds of the instant invention are conveniently prepared using the procedures described generally below and more explicitly described in the Example section thereafter.

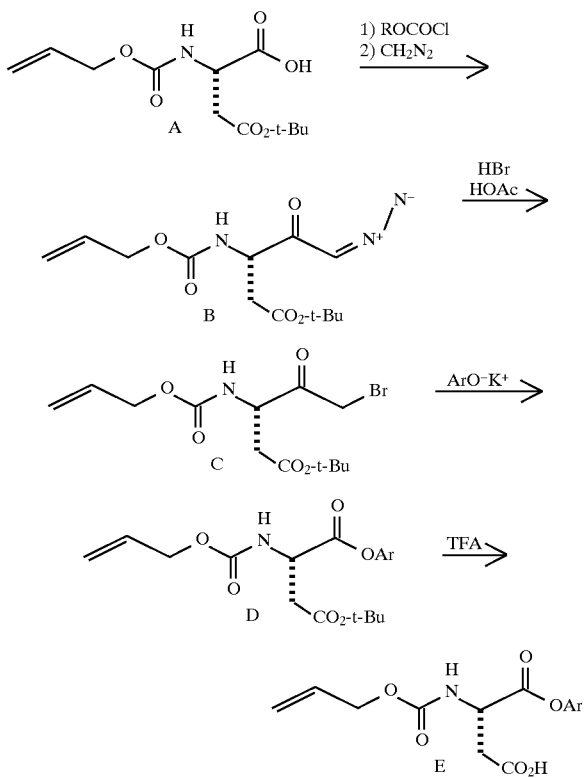

An appropriately N-protected aspartic acid ester A is first treated with an alkyl chloroformate to form the mixed anhydride in situ which is subsequently reacted with excess diazomethane to form the diazomethyl ketone B. Subsequent reaction of B with hydrobromic acid in acetic acid forms the bromomethyl ketone C. Reaction of C with a metal salt of a desired aryloxy compound affects displacement of the bromide to form the aryloxymethyl ketone D. Removal of the t-butyl ester with strong acid (trifluoroacetic acid or hydrochloric acid) will give the desired final product E. In situ removal of the 'Alloc' protecting group with a palladium catalyst and alkyltin hydride in the presence of a carboxylic acid or N-protected amino acid or peptide and a suitable condensing agent(s) will provide other examples.

The compounds of the instant invention of the Formula (I), as represented in the Examples hereinunder shown to exhibit in vitro inhibitory activities with respect to interleukin-1β. In particular, these compounds have been shown to inhibit interleukin-1β converting enzyme from cleaving precusor interleukin-1β as to form active interleukin-1β.

Compounds of the instant invention of Formula (I) are evaluated in vivo by inhibiting LPS-induced fever in rats and by reducing inflammation in carrageenan-induced paw edema in rats by methodology described by R. Heng, T. Payne, L. Revesz, B. Weidmann in PCT W093/09135 (published 13 May 1993).

This invention also relates to a method of treatment for patients (including man and/or mammalian animals raised in the dairy, meat, or fur industries or as pets) suffering from disorders or diseases which can be attributed to IL-1/ICE as previously described, and more specifically, a method of treatment involving the administration of the IL-1/ICE inhibitors of Formula (I) as the active constituents.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix such as interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

For the treatment the above mentioned diseases, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyethylene sorbitan mono-oleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

Additional methods of making compounds of this invention are known in the art such as U.S. Pat. No. 5,055,451, issued to Krantz et al., Oct. 8, 1991 which is hereby incorporated by reference.

EXAMPLE 1

N-Allyloxycarbonyl-3-amino-4-oxo-5-phenoxy-pentanoic acid

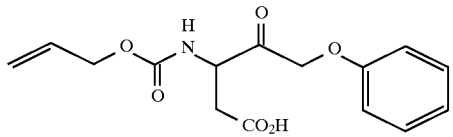

Step A: N-Allyloxycarbonyl-3-amino-5-diazo-4-oxopentanoic acid, t-butyl ester

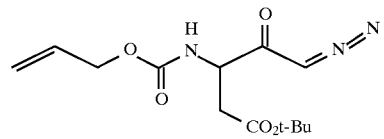

To a solution of N-allyloxycarbonyl-(L)-aspartic acid, β-t-butyl ester (6.23 g, 22.8 mmol) and 4-methyl morpholine (2.63 mL, 23.94 mmol) in 50 mL of freshly distilled dichloromethane at −10° C. was added freshly distilled isobutyl chloroformate (3.04 mL, 23.48 mmol). After 15 min, the solution was filtered and excess ethereal diazomethane was added. The mixture was stirred at 0° C. for 1 h and concentrated. The mixture was purified by medium pressure liquid chromatography (MPLC) on silica-gel (35×350 mm column, eluting with 25% ethyl acetate in hexane) to give the title compound as a pale yellow oil: $^1$H NMR (400 MHz, CDCl$_3$) δ5.91 (1H, m), 5.62 (1H, br s), 5.31 (1H, d), 5.24 (1H, d), 4.61 (2H, br d), 4.50 (1H, m), 2.92 (1H, dd), 2.60 (1H, dd), 1.43 (9H, s).

Step B: N-Allyloxycarbonyl-3-amino-5-bromo-4-oxopentanoic acid, t-butyl ester

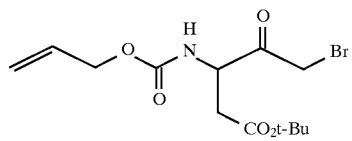

To a solution of N-allyloxycarbonyl-3-amino-5-diazo-4-oxopentanoic acid, β-t-butyl ester in ether was added approximately one equivalent of hydrobromic acid (30% in acetic acid). After 30 min, the solution was diluted with ether and washed three times with water. The combined organic layers were dried over magnesium sulphate, filtered, and concentrated in vacuo. The product was purified by MPLC on silica gel eluted with 20% ethyl acetate in hexane to afford the title compound as a colorless solid:

$^1$H NMR (400 MHz, CD$_3$OD) δ5.93 (1H, m), 5.31 (1H, d), 5.19 (1H, d), 4.69 (1H, t), 4.58 (2H, br d), 4.29 (2H, ABX), 2.82 (1H, dd), 2.63 (1H, 20 dd), 1.43 (9H, s).

Step C: N-Allyloxycarbonyl-3-amino-4-oxo-5-phenoxy-pentanoic acids t-butyl ester

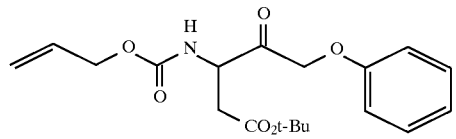

To a solution of phenol (59 mg, 0.628 mmol) in dimethylformamide (5 ml) was added potassium carbonate (87 mg, 0.628 mmol). The mixture was stirred for 5 min, followed by addition of N-allyloxy-3-amino-5-bromo-4-oxo-pentanoic acid, β-t-butyl ester (200 mg, 0.571 mmol). The mixture was stirred for 16 hours at room temperature, then diluted with ethyl acetate and washed with saturated sodium bicarbonate solution. The organic layer was dried over anhydrous sodium sulfate and filtered. The solvent was removed in vacuo and the product purified by flash column chromatography on silica gel eluted with 20% t-butyl methyl ether in hexane to provide the title compound. $^1$H NMR (CD$_3$OD) δ7.25 (2H, m), 6.92 (3H, m), 5.9 (1H, m), 5.22 (2H, m), 4.9 (2H, ABX), 4.7 (1H,t), 4.55 (2H, dd), 2.85 (1H, dd), 2.7 (1H, dd) 1.45 (9H, s).

Step D: N-Allyloxycarbonyl-3-amino-4-oxo-5-phenoxy-pentanoic acid

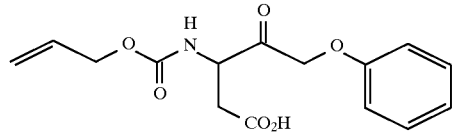

N-allyloxycarbonyl-3-amino4-oxo-5-phenoxy-pentanoic acid, t-butyl ester from Step C (170 mg, 0.467 mmol) was dissolved in dichloromethane (8 ml) and trifloroacetic acid (8 ml) under nitrogen. The resulting mixture was stirred for 15 minutes. The solvent was reduced in vacuo to provide the target compound. $^1$H NMR (CDCl$_3$) δ7.3 (2H, m), 6.92 (3H, m), 5.45 (1H, br.s), 5.2 (2H, m), 4.6 (1H, bs), 4.52 (2H, d), 4.2 (2H, br.s), 2.95 (2H, dbr.); mass spectrum: mile 308(M+ 1)$^+$, 263.9, 213.7, 106.7, 154.7, 119.0.

By following the procedures described in Example 1, Examples 2–9 may be prepared:

EXAMPLE 2

N-Allyloxycarbonyl-3-amino-5-(1-naphthyloxy)-4-oxopentanoic acid

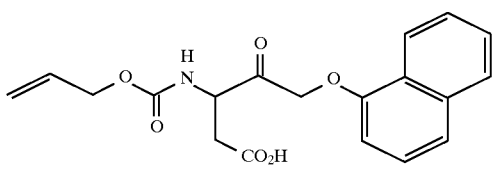

$^1$H NMR(CDCl$_{13}$) δ7.8(1H, m), 7.49(3H, m), 7.31(1H, m), 7.25 (1H, m), 7.15 (1H, m), 5.89 (1H, m), 5.25 (2H, m), 5.0 (2H, ABX), 4.68 (1H, m), 4.55 (2H, m), 3.2 (1H, dd), 3.0 (1H, ddd); mass spectrum: m/e 380 (M+Na)$^+$, 358.1 (M+1)$^+$, 338.8, 196.7, 176.7, 143.9, 119.1.

EXAMPLE 3

N-Allyloxycarbonyl-3-amino-5-(2-naphthyloxy)-4-oxopentanoic acid

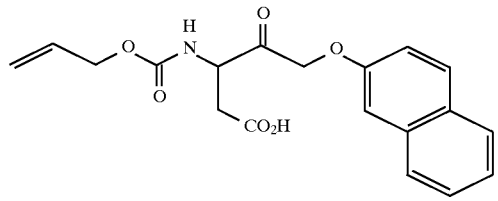

$^1$H NMR(CDCl$_3$) δ7.72 (3H, m), 7.42 (1H, m), 7.35 (1H, m), 7.15 (2H, m), 5.85 (1H, m), 5.25 (2H, m), 5.0 (1H,m), 4.82 (2H, br.s), 4.59 (2H, m), 3.2–2.6 (2H, m); mass spectrum: m/e 380(M+Na)$^+$, 358.1 (M+1)$^+$, 338.8, 196.7, 176.7, 143.9, 119.1.

EXAMPLE 4

N-Allyloxycarbonyl-3-amino-5-(3-aminocarbonyl-2-naphthyloxy)-4-oxopentanoic acid

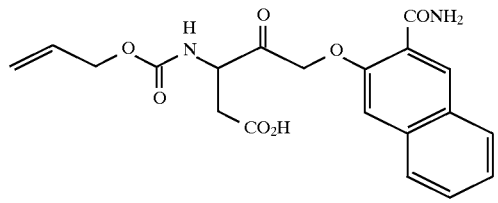

$^1$H NMR (CD$_3$OD) δ7.52 (2H, m), 7.35 (2H, m), 5.9 (1H, m), 5.85 (2H, q), 5.2 (2H, m), 4.72–4.15 (5H,br, m), 2.9 (2H, m); mass spectrum: m/e 423.0 (M+Na)$^+$, 401.8 (M+1)$^+$. 383.8, 365.9, 325.9, 187.7, 170.7, 134.9.

EXAMPLE 5

N-Allyloxycarbonyl-3-amino-5-(3-(N-phenyl)aminocarbonyl-2-naphthyloxy)-4-oxopentanoic acid

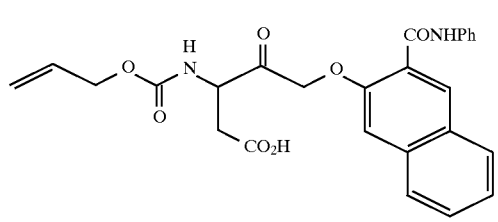

$^1$H NMR (CDCl$_3$) δ7.8 (1H, m), 7.69 (1H, m), 7.45 (2H, m), 7.25 (4H, br m), 7.06 (1H, m), 6.05 (1H, m), 5.9 (1H, m), 5.62 (1H, NH), 5.2 (2H, m), 5.0 (1H, m), 4.7–4.38 (4H, m), 3.1–2.8 (2H, m); mass spectrum: m/e 499.7 (M+Na)$^+$, 477.6 (M+1)$^+$, 459.4, 366.1, 264.0, 182.7, 170.7, 141.9, 115.2.

EXAMPLE 6

N-Allyloxycarbonyl-3-amino-5-(3-cyano-2-naphthyloxy)-4-oxopentanoic acid

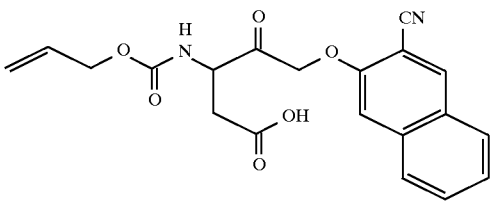

$^1$H NMR (400 MHz, CDCl$_3$) δ8.10 (1H, s), 7.75 (2H, m), 7.58 (2H, m), 7.42 (2H, m), 5.88 (1H, m), 5.15–5.38 (2H, m), 4.85 (2H, s), 4.58 (2H, m), 4.40(1H, m); mass spectrum: m/e M+1(383.1), 365.1, 169.1, 112.1.

EXAMPLE 7

N-Allyloxycarbonyl-3-amino-5-(3-hydroxymethyl-2-naphthyloxy)-4-oxopentanoic acid

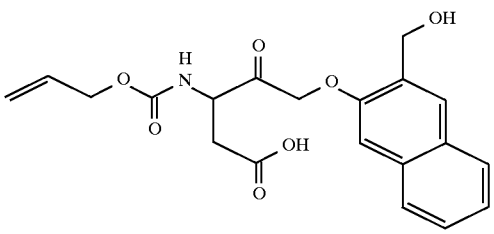

$^1$H NMR (400MHz, CDCl$_3$) δ7.50 (3H, m), 7.42 (2H, m), 7.05 (1H, s), 5.83 (1H, m), 5.20 (2H, m), 4.70–4.92 (2H, m), 4.20–4.61 (5H, brm), 2.60–3.01 (2H, m); mass spectrum: m/e M+K$^+$(426.0), M+Na$^+$(410.0), M$^+$(387.0) 369.9, 352.0, 269.0, 239.0.

EXAMPLE 8

N-Allyloxycarbonyl-3-amino-5-(3-methoxycarbonyl-2-naphthyloxy)-4-oxopentanoic acid

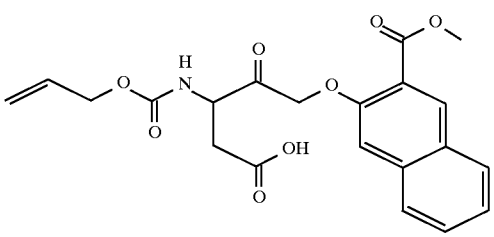

$^1$H NMR (400MHz, CDCl$_3$) δ8.39 (1H, s), 7.82 (1H, d), 7.72 (1H, d), 7.55 (1H, t), 7.42 (2H, m), 7.23( 1H, s), 5.85 (1H, m), 5.50 (1H, s), 5.10–5.40 (1H, m), 4.42–4.70 (4H, m), 4.25 (1H, m), 3.95 (3H, s), 2.75–2.98 (2H, m); mass spectrum: m/e M+Na$^+$(438), M+1 (416), 384, 326, 214, 202, 171, 170.

EXAMPLE 9

N-Allyloxycarbonyl-3-amino-5-(3-(2-hydroxyethyl-1-aminocarbonyl)-2-naphthyloxy)-4-oxopentanoic acid

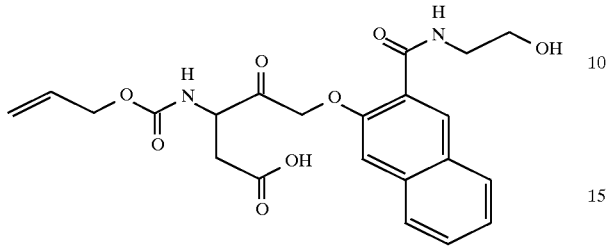

$^1$H NMR (200 MHz, CD$_3$OD) δ8.49 (1H, s), 7.75–7.93 (2H, m), 7.31–7.57 (4H, m), 5.90 (1H, m), 5.00–5.38 (2H, m), 4.18–4.79 (5H, m), 3.82 (2H, t), 3.65 (2H, t), 2.90 (2H, m); mass spectrum: m/e M+1 (444.9), 394.1, 278.9, 218.9, 202.9.

EXAMPLE 10

N-Allyloxycarbonyl-3-amino-5-(3-imidazolyl-2-naphthyloxy)-4-oxopentanoic acid

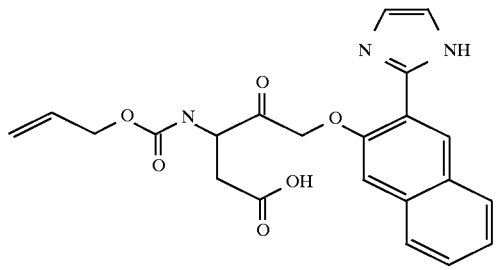

Step A: 3-Benzyloxy-naphthalene-2-carboxylic acid, benzyl ester

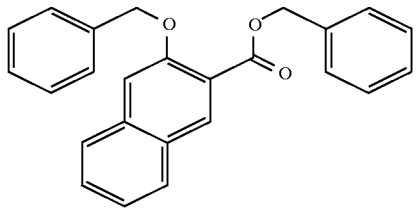

To a solution of 3-hydroxy-naphthalene-2-carboxylic acid (3.76 g, 20 mmol) in dimethylformamide, at 0° C., was added sodium hydride (1.01 g, 42 mmol) 15 minutes later, freshly distilled benzyl bromide (4.98 ml, 42 mmol) was added. After stirring at room temperature under nitrogen for 16 hours, the solution was diluted with ethyl acetate and washed twice with 2N aqueous hydrochloric acid. The organic layer was then dried over anhydrous sodium sulfate and concentrated in vacuo to provide the title compound (7.12 g).

Step B: (3-Benzyloxy-2-naphthyl)methyl alcohol

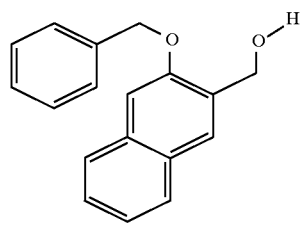

To a solution of 3-benzyloxy-naphthalene-2-carboxylic acid, benzyl ester (7.12 g, 19.34 mmol) in dry dichloromethane at −78° C. was dropwise added diisobutylaluminum hydride (DIBAL-H) (27 ml of 1.5M solution in toluene, 40.6 mmol). The reaction was warmed to room temperature after one hour. Sixteen hours later, the reaction was cooled to 0° C. and was quenched carefully with water. The mixture was diluted with ethyl acetate and washed twice with 2N hydrochloric acid. The organic layer was dried over anhydrous sodium sulfate, filtered and then concentrated in vacuo. The residue was eluted through silica gel with dichloromethane to give the title compound (3.2 g).

Step C: 3-Benzyloxy-naphthalene-2-carboxaldehyde

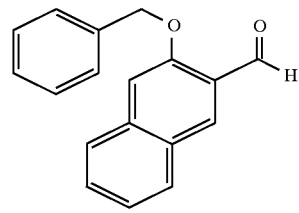

To a solution of (3-benzyloxy-2-naphthyl)methyl alcohol (3.2 g, 12.12 mmol) in dichloromethane was added 4A molecular sieves (6.06 g) and 4-methylmorpholine N-oxide (2.13 g, 18.18 mmol). After 5 minutes, tetrapropylammonium perruthenate (TPAP) (606 mg) was added and the mixture was stirred at room temperature for 3 hours. The mixture was filtered through silica gel eluted with dichloromethane. The eluate was concentrated in vacuo to give the title compound (2.45 g).

Step D: 2-Benzyloxy-3-(2-imidazolyl)naphthalene

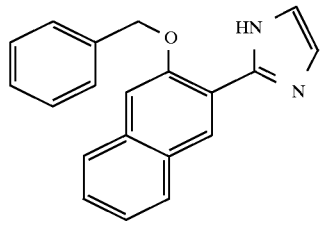

3-Benzyloxy-naphthalene-2-carboxaldehyde (90 mg, 0.34 mmol) and trimeric glyoxal dihydrate (210 mg, 1.02 mmol) were dissolved in 10 ml methanol. The solution was vigorously stirred as concentrated ammonium hydroxide (2 ml) was then slowly added. After 16 hours, the solution was concentrated in vacuo. The residue was eluted with 10% ethyl acetate in hexane through a pad of silica gel to give the title compound (62 mgs).

Step E: 2-Benzyloxy-3-(1-(2-trimethylsilylethoxymethyl)-2-imidazolyl)-naphthalene

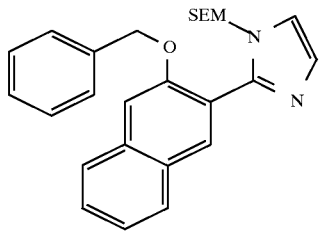

To the solution of 2-benzyloxy-3-(2-imidazolyl) naphthalene (62 mgs, 0.206 mmol) in dry dimethylfonmamide was slowly added sodium hydride (5.2 mg, 0.216 mmol). After 1 hour, 2-(trimethylsilyl)ethoxymethyl chloride (SEM-Cl) (40 ul, 0.227 mmol) was added and the mixture was stirred under nitrogen for 3 hours. The solution was diluted with ethyl acetate and washed 3 times with water. The organic layer was dried over anhydrous sodium sulfate and concentrated in vacuo. The yellow solid was eluted with 20% ethyl acetate in hexane through a pad of silica gel to give the the title compound (40 mgs).

Step F: 3-(1-(2-trimethylsilylethoxymethyl)-2-imidazolyl)-2-naphthol

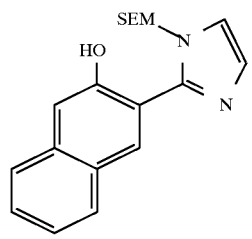

2-Benzyloxy-3-(1-(2-trimethylsilylethoxymethyl)-2-imidazolyl)naphthalene (40 mg) and Pd/C (50 mg) was dissolved in 10 ml methanol. The mixture was stirred vigorously under one atmosphere of hydrogen for 2 hours. The mixture was filtered through celite filter aid, the pad washed with fresh methanol, and the combined eluents concentrated in vacuo. The residue was purified by column chromatography on silica gel eluted with 5% acetone in hexane to afford the title compound (24 mgs).

Step G: N-Allyloxycarbonyl-3-amino-5-(3-imidazolyl-2-naphthyloxy)-4-oxopentanoic acid, t-butyl ester

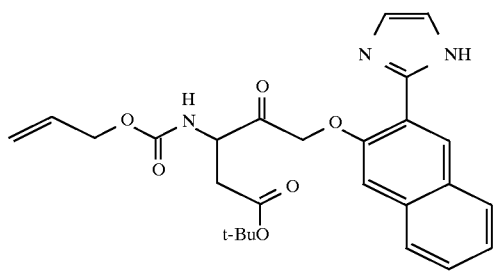

Potassium carbonate (10 mg, 0.071 mmol) and 3-(1-(2-trimethylsilylethoxymethyl)-2-imidazolyl)-2-naphthol (24 mg, 0.071 mmol) were stirred in dimethylformamide (5 ml) under nitrogen for 5 minutes. N-Allyloxycarbonyl-3-amino-5-bromo-4-oxopentanoic acid, t-butyl ester (25 mg, 0.071 mmol) was then added and the mixture was stirred for 16 hours at room temperature under nitrogen atmosphere. The mixture was diluted with ethyl acetate and was successively washed three times with saturated aqueous sodium carbonate solution. The organic layer was dried over sodium sulfate, filtered and concentrated in vacuo. The yellow oil was purified by column chromatography on silica gel eluted with 20% t-butyl methyl ether in hexane to give the title compound (22 mgs).

Step H: N-Allyloxycarbonyl-3-amino-5-(3-imidazolyl-2-naphthyloxy)-4-oxopentanoic acid

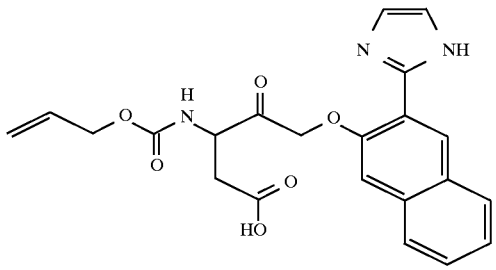

N-Allyloxycarbonyl-3-amino-5-(3-imidazolyl-2-naphthyloxy)-4-oxopentanoic acid, t-butyl ester (22 mg, 0.0360 mmol) was dissolved in dichloromethane (8 ml) and trifluoroacetic acid (8 ml) under nitrogen. After 15 minutes, the solution was concentrated in vacuo to afford the title compound (15 mg): $^1$H NMR (400 MHz, CD$_3$OD) δ8.45 (1H, s), 7.85 (1H, d), 7.78 (1H, d), 7.50 (2H, m), 7.41 (3H, m), 5.50 (1H, m), 5.15–5.38 (4H, m), 4.71(1H, m), 4.60 (2H, m); mass spectrum: m/e M+1 (424.3), 394.5, 172.1, 119.1, 98.1, 86.1.

EXAMPLE 11

N-(N-Acetyl-(L)-tyrosinyl-(L)-valinyl-(L)-alaninyl)-3-amino-5-phenoxy-4-oxopentanoic acid

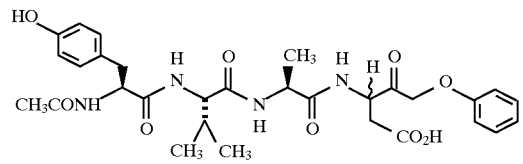

Step A: N-(N-Acetyl-(L)-tyrosinyl-(L)-valinyl-(L)-alaninyl)-3-amino-4-oxo-5-phenoxy-pentanoic acid, t-butyl ester

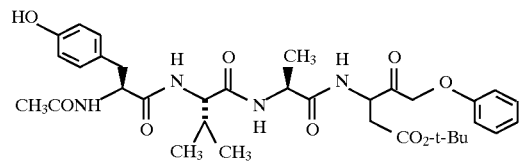

To a solution of N-allyloxycarbonyl-3-amino-4-oxo-5-phenoxy-pentanoic acid, t-butyl ester (from Step C, Example 1) (86 mg, 0.24 mmol) in a 1:1 mixture of dichloromethane:dimethylformamide (6 ml) was added N-acetyl-(L)-tyrosinyl-(L)-valinyl-(L)-alanine (87 mg, 0.26 mmol), N-hydroxybenztriazole (38 mg, 0.28 mmol), 1-(3-dimethylaminopropyl)-3-ethylcarbodiimide hydrochloride (50 mg, 0.26 mmol) and bis(triphenylphosphine) palladium (II) chloride (10 mg). To the stirred mixture, tributyltin hydride (76 ul, 0.28 mmol) was added dropwise. After 16 hours, the mixture was diluted with ethyl acetate and successively washed with 2N hydrochloric acid and saturated sodium bicarbonate solution. The solution was dried over anhydrous sodium sulfate and the solvent was reduced in vacuo. The product was purified by flash column chromatography on silica gel eluted with 5% methanol in dichloromethane to give the title compound. $^1$H NMR (CD$_3$OD) δ7.25 (2H, t), 7.05 (2H, m), 6.95 (3H, m), 6.66 (2H, m), 5.0 (2H, m), 4.75 (1H, tt), 4.55 (1H, m), 4.32 (1H, m), 4.15 (1H, m), 3.1–2.6 (4H, complex), 2.05 (1H, m), 1.98 (3H, ss), 1.42 (9H, s), 1,37 (3H, m), 0.95 (9H, m).

Step B: N-(N-Acetyl-(L)-tyrosinyl-(L)-valinyl-(L)-alaninyl) -3-amino-4-oxo-5-phenoxy-pentanoic acid

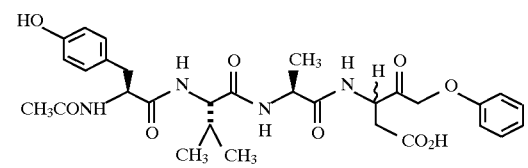

N-(N-Acetyl-(L)-tyrosinyl-(L)-valinyl-(L)-alaninyl)-3-amino-4-oxo-5-phenoxy-pentanoic acid, t-butyl ester (56 mg, 0.086 mmol) was dissolved in a 1:1 mixture of dichloromethane and trifloroacetic acid (20 ml). The mixture was stirred for 15 minutes and then the solvent was reduced in vacuo to afford the title compound. $^1$H NMR (CD$_3$OD), δ7.25 (2H, m), 7.05 (2H, m), 6.95 (3H, m), 6.7 (2H, m), 5.0 (2H, m), 4.72 (1H, tt) 4.58 (1H, m), 4.3 (1H, m), 4.15 (1H, m), 3.1–2.7 (4H, complex), 2.03 (1H, m), 1.89 (3H, m), 1.37 (3H, m), 0.97 (9H, m); mass spectrum: m/e 636.9 (M+K)$^+$, 599.4 (M+1)$^+$, 545.5, 393.8, 375.9, 304.9, 294.9, 205.7, 177.7.

By following the procedures described in Example 11, Examples 12–14 may be prepared:

EXAMPLE 12

N-(N-Carbobenzyloxy-(L)-valinyl-(L)-alaninyl)-3 -amino-5 -(3 -amino-carbonyl-naphthyl-2-oxy)-4- oxo-pentanoic acid, triethylamine salt

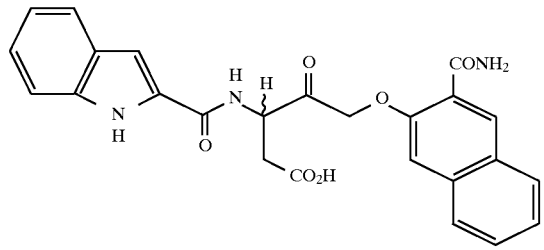

$^1$H NMR (CD$_3$OD) δ7.84 (2H, m), 7.6–7.2 (8H, m), 5.50–5.15 (2H, m), 5.08 (2H, br s), 4.74 (1H, m), 4.40 (1H, m), 3.90 (1H, m), 2.98 (6H, q), 2.90–2.65 (2H, m), 2.08 (1H, br m), 1.41 (3H, d), 1.20 (9H, t), 0.93 (6H, m).

EXAMPLE 13

N-(N-Carbobenzyloxy-(L)-valinyl-(L)-prolinyl)-3- amino-5-(3-amino-carbonyl-naphthyl-2-oxy)-4-oxo- petanoic acid

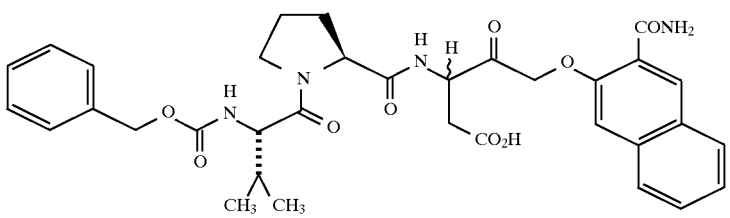

$^1$H NMR (CD$_3$OD) δ7.87 (2H, m), 7.66 (2H, m), 7.55 (2H, m), 7.49–7.25 (5H, m), 5.40, 5.20 (2H, ABq), 5.08 (2H, br s), 4.63, 4.45 (1H, t), 4.30, 4.11 (1H, m), 3.90, 3.70 (1H, br m), 3.11–2.80 (2H, m), 2.26 (1H, br m), 2.17–1.80 (2H, br m), 1.08–0.84 (6H, m), 0.80 (2H, d), 0.68 (2H, d).

EXAMPLE 14

N-(2-indoloyl)-3-amino-5-(3-aminocarbonyl- naphthyl-2-oxy)-4-oxo-pentanoic acid

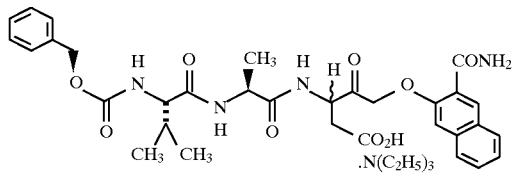

$^1$H NMR (CD$_3$OD) δ7.85–7.0 (1 1H, m), 5.33 (2H, ABq), 5.15 (1H, t), 3.18, 2.95 (2H, dd).

EXAMPLE 15

Inhibition of Interleukin-1β Converting Enzyme (ICE).

A fluorometric assay used to evaluate the inhibition of interleukin-1β converting enzyme (ICE) hydrolysis of a peptide substrate (Ac-Tyr-Val-Ala-Asp-AMC) by the compounds described in Examples 1–15 has been described in detail (N. A. Thornberry et al., *Nature* 1992, 356, 768–774). Briefly, liberation of AMC (aminomethylcoumarin) from the substrate was monitored continuously in a spectrofluorometer using an excitation wavelength of 380 nm and an emission wavelength of 460 nm. Details for determining kinetic constants for reversible and irreversible inhibition are described (N. A. Thornberry et al., *Biochemistry* 1994, 33, 3934–3940).

Inhibition of Interleukin-1β Converting Enzyme (ICE) by Examples 1–14

| Example No. | Ki (μM) | (± S.E.) | $k_{on}$ ($M^{-1}s^{-1}$) | (± S.E.) |
|---|---|---|---|---|
| 1 | 3.5 | (0.6) | | |
| 2 | 9.5 | (2.) | | |
| 3 | 5.0 | (1.) | | |
| 4 | 0.3 | (0.1) | | |
| 5 | 0.5 | (0.1) | | |
| 6 | 0.62 | (0.1) | 4500 | (900) |
| 7 | 1.2 | (0.2) | | |
| 8 | 2.6 | (0.5) | | |
| 9 | 0.52 | (0.1) | 1000 | (200) |
| 10 | 0.09 | (0.02) | 12,000 | (2,400) |
| 11 | 0.003 | (0.0005) | | |
| 12 | | | 430,000 | (86,000) |
| 13 | | | 340,000 | (68,000) |
| 14 | | | 390 | (78) |

What is claimed is:

1. A compound of Formula I

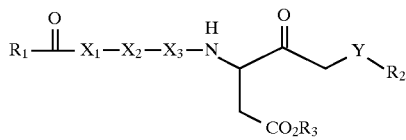

or a pharmaceutically acceptable salt thereof wherein:

$R_1$ is
(a) allyloxycarbonyl;
(b) acetyl;
(c) indoloyl; or
(d) carbobenzyloxy;

$R_2$ is
(1) phenyl; or
(2) naphthyl, unsubsituted or ortho-substituted with —$CONH_2$, —CONHPh, —CN, —$CH_2OH$, —$CO_2Me$, 2-hydroxyethyl-1-aminocarbonyl, or 3-imidazolyl;

$R_3$ is
(a) hydrogen, or
(b) $C_{1-6}$ alkyl;

$X_1$, $X_2$, and $X_3$ are independently selected from the group consisting of
(a) a single bond, and
(b) an amino acid selected from the group consisting of L- and D- forms of the amino acids tyrosine, valine, alanine, and proline;

Y is O.

2. A compound selected from the group consisting of:
a) N-Allyloxycarbonyl-3-amino-4-oxo-5-phenoxy-pentanoic acid;
b) N-Allyloxycarbonyl-3-amino-5-(1-naphthyloxy)-4-oxopentanoic acid;
c) N-Allyloxycarbonyl-3-amino-5-(2-naphthyloxy)-4-oxopentanoic acid;
d) N-Allyloxycarbonyl-3-amino-5-(3-aminocarbonyl-2-naphthyloxy)-4-oxopentanoic acid;
e) N-Allyloxycarbonyl-3-amino-5-(3-(N-phenyl)aminocarbonyl-2-naphthyloxy)-4-oxopentanoic acid;
f) N-Allyloxycarbonyl-3-amino-5-(3-cyano-2-naphthyloxy)-4-oxopentanoic acid;
g) N-Allyloxycarbonyl-3-amino-5-(3-hydroxymethyl-2-naphthyloxy)-4-oxopentanoic acid;
h) N-Allyloxycarbonyl-3-amino-5-(3-methoxycarbonyl-2-naphthyloxy)-4-oxopentanoic acid;
i) N-Allyloxycarbonyl-3-amino-5-(3-imidazolyl-2-naphthyloxy)-4-oxopentanoic acid;
j) N-(N-Acetyl-(L)-tyrosinyl-(L)-valinyl-(L)-alaninyl)-3-amino-5-phenoxy-4-oxopentanoic acid;
k) N-(N-Carbobenzyloxy-(L)-valinyl-(L)-alaninyl)-3-amino-5-(3-aminocarbonyl-naphthyl-2-oxy)-4-oxopentanoic acid, triethylamine salt;
l) N-(N-Carbobenzyloxy-(L)-valinyl-(L)-prolinyl)-3-amino-5-(3-aminocarbonyl-naphthyl-2-oxy)-4-oxopentanoic acid; and
m) N-(2-indoloyl)-3-amino-5-(3-aminocarbonyl-naphthyl-2-oxy)-4-oxo-pentanoic acid.

3. A compound which is:
N-Allyloxycarbonyl-3-amino-5-(3-imidazolyl-2-naphthyloxy)-4-oxopentanoic acid or a pharmaceutically acceptable salt thereof.

4. A pharmaceutical composition comprising a compound of claim 1 along with a pharmaceutically acceptable diluent.

5. A pharmaceutical composition comprising a compound of claim 2 along with a pharmaceutically acceptable diluent.

6. A method of inhibiting Interleukin-1 converting enzyme in a patient in need thereof comprising administering an enzyme inhibiting amount of a compound of claim 1.

7. A method of inhibiting Interleukin-1 converting enzyme in a patient in need thereof comprising administering an enzyme inhibiting amount of a compound of claim 2.

* * * * *